US007659236B2

(12) United States Patent
Lee et al.

(10) Patent No.: US 7,659,236 B2
(45) Date of Patent: Feb. 9, 2010

(54) BAR COMPOSITION COMPRISING THERMOCHROMIC PIGMENT OR DYE SIGNALLING BENEFIT AGENT RELEASE OR OTHER USE

(75) Inventors: Christine Marie Nixon Lee, Oakville, CT (US); Michael Augustine Brennan, Sandy Hook, CT (US); Vivek Subramanian, Southbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 237 days.

(21) Appl. No.: 11/736,871

(22) Filed: Apr. 18, 2007

(65) Prior Publication Data

US 2008/0261843 A1 Oct. 23, 2008

(51) Int. Cl.
*A61K 7/00* (2006.01)

(52) U.S. Cl. ....................... 510/141; 510/146; 510/153; 510/155

(58) Field of Classification Search ....................... None
See application file for complete search history.

(56) References Cited

U.S. PATENT DOCUMENTS 3,673,294 A 6/1972 Matthaei
4,663,070 A 5/1987 Dobrovolny et al.

FOREIGN PATENT DOCUMENTS

| | | | |
|---|---|---|---|
| EP | 0 418 049 | A | 3/1991 |
| GB | 2 305 932 | A | 4/1997 |
| JP | 01-308499 | A | 12/1989 |
| WO | 01/12150 | A1 | 2/2001 |
| WO | 02/02729 | A | 1/2002 |
| WO | 06/137955 | A | 12/2006 |

OTHER PUBLICATIONS

Co-pending application: Applicant: Lee et al. U.S. Appl. No. 11/736,901, filed Apr. 18, 2007.
International Search Report on International Application No. PCT/EP2008/054092 dated Aug. 4, 2008.
International Preliminary Report on Patentability on International Application No. PCT/EP2008/054092dated May 25, 2009.
US 6,290,977, 09/2001, Friars et al. (withdrawn)

*Primary Examiner*—Necholus Ogden, Jr.
(74) *Attorney, Agent, or Firm*—Ronald A. Koatz

(57) ABSTRACT

The invention relates to bar compositions comprising thermochromatic pigment or dye signaling temperature and/or benefit agent release. In a preferred embodiment, the pigment is introduced in the form of a separate domain (e.g., separate chips) which separate chip or chips is combined with a surfactant-containing chips to form the final bar.

4 Claims, 1 Drawing Sheet

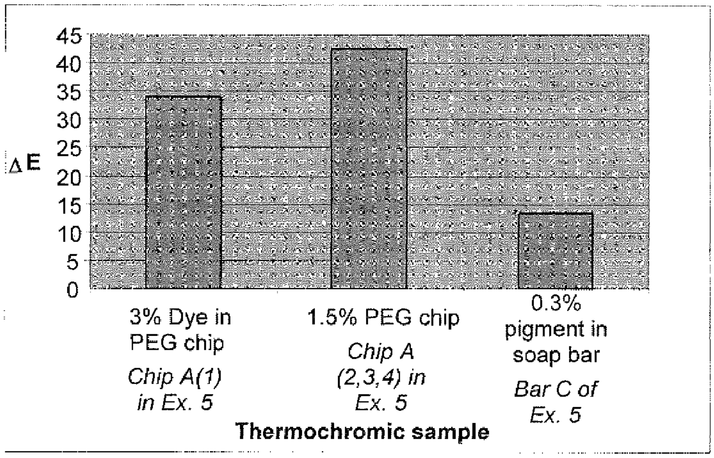

This figure shows ΔE for PEG-8000 chip containing 3% and 1.5% thermochromic pigment (chip A(1) of Example 5 is 3% dye in chip and chips A(2) – A(4) have 1.5% dye in chip) compared to ΔE for soap bar containing 0.3% PEG uniformly distributed throughout the bar (bar C in Example 5). For concentrated domain (chips A(1) – A(4)), only chip was measured whereas for uniform dispersal (Bar C), entire bar can be measured for ΔE values.

Fig. 1

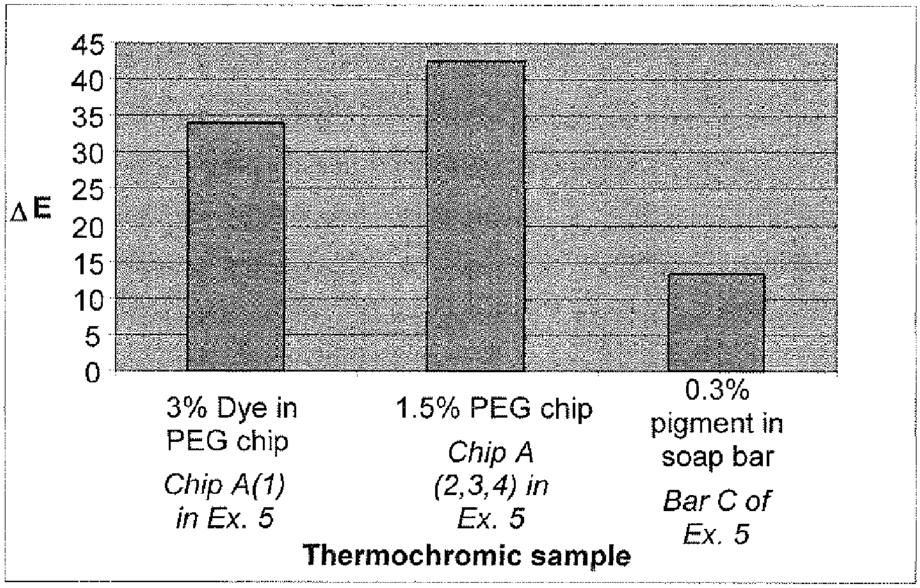

This figure shows ΔE for PEG-8000 chip containing 3% and 1.5% thermochromic pigment (chip A(1) of Example 5 is 3% dye in chip and chips A(2) – A(4) have 1.5% dye in chip) compared to ΔE for soap bar containing 0.3% PEG uniformly distributed throughout the bar (bar C in Example 5). For concentrated domain (chips A(1) – A(4)), only chip was measured whereas for uniform dispersal (Bar C), entire bar can be measured for ΔE values.

BAR COMPOSITION COMPRISING THERMOCHROMIC PIGMENT OR DYE SIGNALLING BENEFIT AGENT RELEASE OR OTHER USE

FIELD OF THE INVENTION

The invention relates to bar compositions comprising a thermochromic pigment or dye. The dye changes color upon elevation of water temperatures during use/wash and change in color may be used, for example, to signal water temperature at time of dye color change or, preferably, to signal release of benefit agent (e.g., moisturizer, perfume) from bar. In a preferred embodiment, the pigment or dye is found in concentrated domains (e.g., within a delivery chip) rather than being dispersed through the bar composition. This helps to highlight the color change at the requisite temperature. The concentrated domains also help mask the fact that benefit agents may be non-ideally mixed into a bar base, and highlights them as visible benefit agent particles rather than a processing deficiency.

BACKGROUND

Thermochromic materials or pigments, i.e., pigments which change color at defined temperature ranges, are not themselves novel. For example, such thermochromatic pigments are used in children's bath toys or baby spoons to indicate when temperature of bath water or of child's food is too hot.

WO 01/12150 A1 (assigned to Unilever) discloses cosmetic compositions which comprise (i) an agent which will interact with water and cause a temperature change in the cosmetic; (ii) a thermochromatic substance which changes color in response to temperature change; and (iii) a pharmaceutically acceptable vehicle to deliver (i) and (ii) (e.g., moisturizers such as polyols). Although emulsifiers are optionally disclosed, the cosmetic compositions are not cleansing compositions (e.g., comprising minimum levels of surfactant cleanser). Further, the compositions require an agent which interacts with water to cause a temperature charge. In the subject invention, no such agent is required and the thermochromatic substance is simply a cue that a certain water temperature has been reached (and/or that benefit agent is released at said water temperature).

U.S. Pat. No. 6,290,977 to Friars et al. discloses flowable topical personal care compositions comprising (i) a thermochromatic pigment capable of color change between 20° C. and 40° C.; and (ii) a personal care active, said components (i) and (ii) being stably dispersed in a vehicle. There is no disclosure of a thermochromatic pigment in a solid aqueous bar (e.g., having 3 to 20% by wt., preferred 5 to 18% by wt. water). There is further no disclosure of concentrating the indicator dye (encapsulated or non-encapsulated dye) in regions or domains (e.g., in a polyalkylene chip) such that less of the dye can be used and/or where imperfect mixing of benefit agents (e.g., applied at lower temperature in the formulation/mixing process) can be masked and indeed presented as a positive.

BRIEF DESCRIPTION OF THE INVENTION

Unexpectedly, applicants have found that encapsulated and/or non-encapsulated pigment or dye can be used in solid, surfactant containing cleansing compositions (e.g., bars) having 3 to 20%, preferably 5 to 18% water. The color change of these thermochromatic pigments or dyes is triggered when water temperature at the bar surface reaches a certain defined temperature and thus can be used as a cue that specific water temperatures are reached and/or that certain benefit agents (which release when defined temperature is achieved and bar starts to dissolve) are released at a certain temperature.

In a preferred embodiment of the invention, the pigment or dye (in encapsulated and/or non-encapsulated form) is concentrated in certain regions or domains of the bar. This can be accomplished, for example, by enclosing or formulating the dye in a separate chip composition (e.g., polyalkylene glycol chip). This achieves the dual advantage of requiring less overall dye to be used to accomplish the same color-changing affect (compared to if the dye were evenly dispersed throughout the bar); and of allowing certain benefit agents to be formulated late in the process (when mixing temperature is lower) where the benefit agent will be generally poorly mixed because of lower mixing temperatures. More specifically, rather than focusing on the extent to which the chips may be mixed, the presence of chips or domains containing the dye will be highlighted and used as a positive signal that the benefit agents will be released at a certain temperature as noted above.

More specifically, in one embodiment of the invention, the invention comprises solid bar compositions comprising:

(1) 5 to 85% by wt., preferably 10 to 80% by wt., more preferably 15 to 75% by wt. of a surfactant selected from the group consisting of anionic, nonionic, amphoteric, and cationic surfactants and mixtures thereof;

(2) 0 to 50%, preferably 1 to 20% by wt. structurant (e.g., sodium isethionate/sodium stearate);

(3) 0 to 30% by wt. free fatty acid;

(4) 0.1 to 10% by wt. of a thermochromatic pigment or dye; and (5) 0 to 25%, preferably 1 to 20%, more preferably 1 to 15% by wt. benefit agent.

Compositions such as described above may include compositions in which the surfactant is anionic such as alkanoyl isethionate (e.g., alkali metal cocoyl isethionate) and where said isethionate comprises 30-70%, preferably 40-60% of the bar composition. In one embodiment such bars may have, in addition to alkanoyl isethionate, 20-30% free fatty acid, 3 to 10% sodium isethionate and 5 to 15% soap as structurant. In another embodiment, a bar may comprise 20-40% alkanoyl isethionate and may comprise 15 to 30% polyalkylene glycol as structurant.

Bar compositions may be predominantly fatty acid soap composition (comprising, for example 50-85% fatty acid soap, fillers and water), composites comprising mixture of fatty acid soap and free fatty acid (such as described in U.S. Pat. No. 6,846,287 to Farrell which may comprise, for example, 10 to 70%, preferably 30 to 60% soap and 10 to 65% free fatty acid. Compositions may also comprise 30 to 70% fatty acid soap and 15 to 25% alkanoyl isethionate as described in U.S. Pat. No. 4,663,070 to Dobrovolny et al.

It should be noted that, if the pigment is delivered as a separate chip or other concentrated domain (see below), separate chips with which the pigment-containing chips are mixed need themselves not, and preferably do not, contain pigment.

In a second embodiment, the bar compositions are made (e.g., are extruded) from combination of surfactant-containing chip (which, as noted, need contain no pigment) and a pigment-containing chip wherein the pigment-containing chip comprises 5% to 40% of the chips forming the final bar composition and surfactant-containing chips comprise 95 to 60% of the chips forming the final bar composition.

The pigment containing composition in turn comprises 40 to 99.9% of the chip composition water soluble structurant (e.g., polyalkylene glycol chip) which structurant may also function as intended benefit agent; 0 to 40% of chip composition other benefit agent; 0.1 to 25% of chip composition pigment or dye (capsulated or un-encapsulated); and 0 to 10% of chip composition water. A typical chip composition comprises only structurant (e.g., PEG) and pigment. In one embodiment (when surfactant chip and pigment chip are not intimately mixed), these pigment containing chip compositions form concentrated regions (ranging from 50 μm to 1 cm in its largest dimension) of the dye/pigment through the final bar composition In a third embodiment of the invention, the invention relates to a method of signifying or cueing to a consumer that rinse water (used in wash or bath, for example) has achieved a desired temperature (e.g., temperature at which thermochromatic pigment changes colors) and/or that benefit agent or agents are released when such temperature is achieved.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term “about”. Similarly, all percentages are weight/weight percentages of the total composition unless otherwise indicated. Numerical ranges expressed in the format “from x to y” are understood to include x and y. When for a specific feature multiple preferred ranges are described in the format “from x to y”, it is understood that all ranges combining the different endpoints are also contemplated. Where the term “comprising” is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

BRIEF DESCRIPTION OF THE FIGURES

FIG. 1 is a plot showing change in ΔE (L*, a*, b*) scores (showing change in colors) immediately after thermochromatic-containing material is rinsed under warm water (e.g., greater than about 40° C.). Specifically, PEG (polyethylene glycol) chips were prepared containing either 3% or 1.5% thermochromatic pigment. The chips, when mixed into the bar base at 10% chip by weight (total 0.3% pigment in bar), remained intact so that intensity of the color change of the chips shown in FIG. 1 matched the intensity observed by the user (columns 1 and 2 of FIG. 1). This is a preferred embodiment of the invention. By contrast, when 0.3% pigment was mixed uniformly into the bar base, the color change in intensity was lower (column 3 of FIG. 1) than when the pigment was localized in the chip.

DETAILED DESCRIPTION OF THE INVENTION

In its broadest form, the subject invention relates to solid bar compositions comprising thermochromatic pigments or dyes. The dyes, which may be encapsulated or non-encapsulated can be used as indicators that rinse temperatures at which user is washing has reached a certain threshold and/or to signal that, at such temperature, a benefit agent or other desired agent (e.g., occlusives, humectants, elastomers, polymers) is being released. That is, the color change cues or signals that a benefit agent is released as a positive signal to the user.

In a preferred embodiment, the dye or pigment is maintained in concentrated regions within the bar composition (e.g., by using a chip, such as polyalkylene glycol chip, to envelop the dye and maintain it in these regions where the chip is found). This allows for far less dye to be used while providing the same visual cue. It also permits for formulators to formulate benefit agents at cooler temperatures. While, normally, the benefit agents which are not intimately mixed (because of later additions and cooler temperatures) might be seen as a negative by a consumer, formulating chips with thermochromatic dye to signal delivery of benefit agents overcomes or masks any negative perception because the areas where the color changes are instead seen as a positive indicator.

As far as applicants are aware, no such thermochromatic chips have been formulated in solid bar compositions (either single type of chips, forming uniform dispersion of dye, or as combination two or more types of chips forming concentrated domains).

In should be understood that the dyes may be formulated in a broad variety of solid bar formulations ranging from bars which are pure soap bar compositions (e.g., 50-85% fatty acid salt), to bars which are entirely synthetic surfactant compositions, to bars which are mixtures of synthetic surfactant and soap in a broad variety of ratios. The crux of the invention is not the base formulation, but use and release of dye in such solid bar compositions.

Thus, the bar compositions of the invention may comprise:

(1) 5 to 85% by wt., preferably 10 to 80% by wt., more preferably 15 to 75% by wt. of a surfactant selected from the group consisting of anionic, nonionic, amphoteric, and cationic surfactant and mixtures thereof, (2) 0 to 50% by wt., preferably 1 to 30% by wt. structurant;

(3) 0 to 30%, preferably 1 to 25% by wt. free fatty acid;

(4) 0.1 to 10% by wt. thermochromatic pigments or dye; and (5) 0 to 25%, preferably 1 to 20%, more preferably 1 to 5% by wt. benefit agent.

Examples of compositions which may be used include, but are certainly not limited, as follows (all percentages by weight):

Composition A

| | |
|---|---|
| Coco fatty acid isethionate | 40-60% |
| Free fatty acid | 20-30% |
| Sodium isethionate | 3-7% |
| Soap | 8-10% |
| Perfume, water, minors | to balance |

Composition B

| | |
|---|---|
| Cocoyl isethionate | 20-40% |
| Polyethylene polyol (PEG 8000) | 15-35% |
| Free fatty acid | 15-25% |
| Alkali metal stearate | 2-12% |

-continued

| | |
|---|---|
| Cocoamidopropyl betaine | 1-5% |
| Sodium isethionate | 5-10% |
| Minors, water | to balance |

Composition C

| | |
|---|---|
| Fatty acid soap | 40-60% |
| Cocoyl isethionate | 15-25% |
| Stearic acid | 5-8% |
| Alkali metal isethionate | 3-8% |
| Free fatty acid | 1-3% |
| Minors, water | to balance |

Composition D

| | |
|---|---|
| Free acid soap | 60-90% |
| Water & minors | to balance |

The dye of component (4) above may be introduced to the bar by dispersing it throughout the bar (e.g., when a single chip is used and dye is found in all the chips), or it may be introduced by forming pigment-containing chips which are separate from the surfactant-containing chips. The pigment-containing chips then help form concentrated regions of color in the final bar (when heated by contact with water and released). This is a preferred embodiment of the subject invention.

The surfactants noted below are found in all the chips used to form a bar if only one type of chip is used; or in surfactant-containing chips (which generally have no pigment) if separate pigment-containing chips are used.

Each component is described in greater detail below.

Anionic Surfactants

The anionic surfactant may be, for example, an aliphatic sulfonate, such as a primary alkane (e.g., $C_8$-$C_{22}$) sulfonate, primary alkane (e.g., $C_8$-$C_{22}$) disulfonate $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$-$C_{22}$ alkyl and M is a solubilizing cation;

amido-MIPA sulfosuccinates of formula $$RCONH(CH_2)CH(CH_3)(SO_3M)CO_2M$$

where M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $R^2CONR^3CH_2CH_2SO_3M$ wherein $R^2$ ranges from $C_8$-$C_{20}$ alkyl, $R^3$ ranges from $C_1$-$C_4$ alkyl and M is a solubilizing cation.

Another class of anionics are carboxylates such as follows;

$$R—(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$-$C_{18}$ acyl isethionates. These esters are prepared by reaction between alkali metal isethionate with mixed aliphatic fatty acids having from 6 to 18 carbon atoms and an iodine value of less than 20. Typically, at least 75% of the mixed fatty acids have from 12 to 18 carbon atoms and up to 25% have from 6 to 10 carbon atoms.

Another surfactant which may be used are $C_8$ to $C_{22}$ neutralized fatty acids (soap). Preferably, the soap used are straight chain, saturated $C_{12}$ to $C_{18}$ neutralized fatty acids.

If bar is a predominantly synthetic bar, anionic (e.g., acyl isethionate) may comprise 30 to 70% of bar. In pure soap bar, fatty acid soaps may comprise 60-90% of bar.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$\begin{array}{c} (R^3)_x \\ | \\ R^2—Y^{(+)}—CH_2—R^4Z^{(-)} \end{array}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

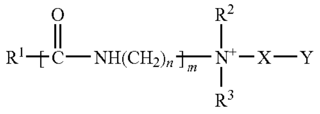

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $-CO_2-$ or $-SO_3-$

Suitable amphoteric detergents within the above general formula include simple betaines of formula:

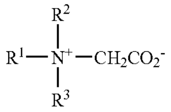

and amido betaines of formula:

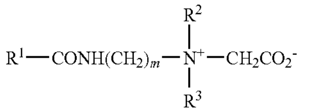

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

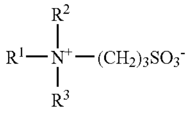

or

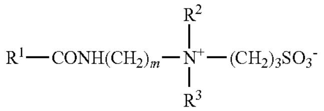

where m is 2 or 3, or variants of these in which $-(CH_2)_3SO_3^-$ is replaced by

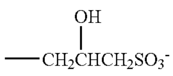

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 5% to 15% of the composition.

In addition to one or more anionic and optional amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Structurant

The structurant is typically a longer chain (e.g., $C_{18}$) fatty acid soap such as, for example, alkali metal stearate. While in a pure soap bar, longer chain fatty acids can be defined both as anionic surfactant and structurant, in a bar which is primarily a synthetic surfactant bar (e.g., containing 30-70% synthetic such as acyl isethionates), these essentially insoluble fatty acids are more typically designated as structurants.

As indicated previously, however, the subject invention is not defined by the base cleansing system in which dyes are found (whether soaps, synthetic or mixture of the two), but on the use of the thermochromatic dye at all in solid, aqueous based cleansing systems.

When defined as distinct from the surfactant system, structurant (e.g., $C_{16}$ to $C_{22}$ chain length fatty acids and fatty acid soaps) may comprise 0 to 50%, preferably 0 to 30% by wt., more preferably 1 to 25% or 1 to 15% of the bar composition. For example, in one embodiment, the bar comprises 40-60% anionic (e.g., cocoyl isethionate), 20-30% free fatty acid (longer chain of which can act as structurant) and 0-10% by wt. sodium stearate.

It should be noted that in some bar compositions of the invention it is also possible to use less anionic than would be typically used in a synthetic bar (e.g., 20 to 40% versus 30 to 70%) and to use water soluble structurants (e.g., polyalkylene oxide or polyalkylene glycols) as structurant rather than more insoluble fatty acid structurants such as $C_{16}$ to $C_{22}$ fatty acid or fatty acid soaps. Such water soluble structurant may comprise from 10 to 40% by wt. of the bar. Such bars are described, for example, in U.S. Pat. No. 6,028,042 to Chambers.

Free fatty acids of 8-22 carbon atoms may also be desirably incorporated within the compositions of the present invention. Some of these fatty acids are present to operate as superfatting agents and others as skin feel and creaminess enhancers. Superfatting agents enhance lathering properties and may be selected form fatty acids of carbon atoms numbering 8-18, preferably 10-16, in an amount up to 35% by weight, preferably 1 to 25% by wt. of the composition. Skin feel and creaminess enhancers, the most important of which is stearic acid, may also desirably present in these compositions.

Mildness Enhancer

Skin mildness improvers which may also be used in the composition of the invention are salts of isethionate. Effective salts cations may be selected from the group consisting of alkali metal, alkaline earth metal, ammonium, alkyl ammonium and mono-, di- or tri-alkanolammonium ions. Specifically preferred cations include sodium, potassium, lithium, calcium, magnesium, ammonium, triethylammonium, monoethanolammonium, diethanolamomnium or tri-ethanolammonium ions.

Particularly preferred as a mildness improver is simple, unsubstituted sodium isethionate of the general formula R $CHOH_2CH_2SO_3Na$ wherein R is hydrogen.

The skin mildness improver will be present from about 0% to about 30%. Preferably, the mildness improver is present from about 1% to about 25%, more preferably from about 2% to about 15%, optimally from 3% to 10% by weight of the total composition.

Reversible Thermochromic Materials

The thermochromic materials used herein may be in the form of fine pigment particles, micro-encapsulated materials, or molecular materials and, among these, fine pigment particles are preferred. It should be understood that the term thermochromic material is used herein to mean any and all thermochromic materials inclusive of quasi-reversible and pseudo-thermochromic materials which show a hysteresis of thermochromism. The materials are generally not thermochromic liquid crystal materials and are preferably in the form of pigment particles.

Suitable thermochromic materials, for example, are available from Clark R&D Ltd., Rolling Meadows, Ill. under the trademark ColorTell®. Clark R&D uses pigments supplied by Matsui Shikiso Chemical Co., Ltd., (Kyoto, Japan), and then recreates the different forms of inks, i.e., paraffin wax based inks, water dispersion inks, mineral oil dispersion inks, etc. Clark typically prints these inks onto plastic cups, baby bottles, beverage containers, thermometers, or spoons, so that the printed area may change color, e.g., to say hot or cold. ColorTell® Printing Inks are available in 12 basic colors and in unlimited colors when combined with non-thermochromic materials. All of the inks are available in 18 different temperature ranges varying from 50 to 338° F. Inks can go from a low temperature color to colorless at a higher temperature, or go from low temperature color to a higher temperature. ColorTell® inks are low in volatile organic compounds (VOC) as a result of being formulated with water, and they are virtually odor free. All of the inks are non-toxic upon drying and can be applied to almost any type of substrate. Other suppliers of thermochromic pigments include H. W. Sands Corp., Jupiter, Fla. and Cleveland Pigment and Color, Akron, Ohio.

Not until the present invention was the possibility considered of formulating a solid bar composition with such materials in order to cue changes in the temperature and/or delivery of benefit agent, Reversible thermochromic compositions are known which are constituted of a solubilized mixture containing essentially a reaction medium for causing reversible electron exchange between an electron-donating coloring organic compound and an electron-accepting organic compound in a specific temperature range as disclosed in U.S. Pat. Nos. 4,028,118; 4,732,810; 4,865,648; 4,720,301; 4,957,949; 4,554,565; 4,425,161; and 4,421,560.

Additional examples of reversible thermochromic materials (materials of our invention are typically reversible) that can be used in the present invention include those disclosed in U.S. Pat. No. 5,281,570 (Hasegawa, et al.) entitled "Thermochromic Materials" and teaching a microencapsulated reversible thermochromic material comprising: (a) an electron donative color former; (b) a sulfide, sulfoxide or sulfone containing a hydroxy phenyl radical; and (c) a chemical compound selected from alcohols, esters, ethers, ketones, carboxylic acids or acid amides; U.S. Pat. No. 4,425,161 (Shibahashi, et al.) entitled "Thermochromic Materials" teaching a thermochromic material comprising (a) an electron-donating, chromatic organic compound, (b) a compound capable of reversibly accepting an electron or electrons from the electron-donating, chromatic organic compound, (c) a compound controlling the temperature and sensitivity of coloration/discoloration of the thermochromic material and (d) a N-radial, P-radical, O-radical or S-radical cationic compound having an aromatic ring or rings which improves by light-fastness; U.S. Pat. No. 4,717,710 (Shimizu, et al.) entitled "Thermochromic Composition" teaching a thermochromic composition comprising (1) an electron-donating chromogenic material, (2) a 1,2,3-triazole compound, (3) a weakly basic, sparingly soluble azomethine or carboxylic acid primary amine salt, and (4) an alcohol, amide or ester serving as a solvent; and U.S. Pat. No. 5,558,700 (Shibahashi, et al.) entitled "Reversible Thermochromic Composition" teaching a reversible thermochromic composition comprising a solubilized mixture of three components of (a) an electron-donating color-developing organic compound selected form pyridine types, quinazoline types, and bisquinazoline types of compound, (b) an electron-accepting compound for the electron-donating color-developing organic compound, and (c) a compound serving as a reaction medium for causing reversibly an electron exchange reaction between the components (a) and (b) within a specified temperature range, the composition developing a fluorescent color of yellow, yellowish or orange, reddish orange, or red with a high color density and high color brightness, yet gives no residual color under non-color developing conditions, and has remarkably improved light resistance.

The acid-responsive chromogenic substance in the thermochromic material includes tirphenylmethanephthalide compounds, phthalide compounds, phthalan compounds, acylleucomethylene blue compounds, fluoran compounds, triphenylmethane compounds, diphenylmethane compounds, spiropyran compounds and so on. Among species of such compounds are 3,6-dimethoxyfluoran, 3,6-dibutoxyfluoran, 3-diethylamino-6,8-dimethylfluoran, 3-chloro-6-phenylaminofluoran, 3-diethylamino-6-methyl-7-chlorofluoran, 3-diethylamino-7,8-benzofluoran, 2-anilino-3-methyl-6-diethylaminofluoran, 3,3',3"tris(p-dimethylaminophenyi)phthalide, 3,3'-bis(p-dimethylaminophenyl)-phthalide, 3-diethylamino-7-phenylaminofluoran, 3,3-bis(p-diethylaminophenyl)-6-dimethylaminophthalide, 3-(4-diethyl-aminophenyl)-3-(1-ethyl-2-methylindol-3-yl)phthalide, 3-(4-diethylamino-2-methyl)phenyl-3-(1,2-dimethylindol-3-yl) phthalide, 2'-(2-chloroaniline)-6'dibutylaminospiro-[phthalido-3,9'-xanthene] and so on.

The acidic substance mentioned above includes, 1,2,3-benzotriazole compounds, phenol compounds, thiourea compounds, oxo-aromatic carboxylic acids and so on. Among specific examples of such compounds are 5-butylbenzotriazole, bisbenzotriazole-5-methane, phenol, nonylphenol, bisphenol A, bisphenol F, 2,2'-biphenol, beta.-naphthol, 1,5,-dihydroxynaphthalene, alkyl p-hydroxybenzoates, phenol resin oligomer and so on.

The amount of the acidic substance may be in the range of about 0.1 to 50 parts by weight per part by weight of the acid-responsive chromogenic substance.

Any of the thermochromic materials each containing an acid-responsive chromogenic substance and an acidic substance are preferably diluted with a solvent before use. The use of a solvent renders the material responsive to change in temperature with greater sensitivity and definition. The solvent which can be used for the thermochromic material includes, among others, alcohols, alcohol-acrylonitrile adducts, azomethine compounds, esters and so on, Among specific examples of the solvent are decyl alcohol, lauryl alcohol, myristyl alcohol, cetyl alcohol, stearyl alcohol, behenyl alcohol, lauryl alcohol-acrylonitrile adduct, myristyl alcohol-acrylonitrile adduct stearyl alcohol-acrylonitrile adduct, benzylidene-p-toluidine, benzylidene-butylamine, octyl caprate, decyl caprate, myristyl caprylate, decyl laurate, lauryl laurate, myristyl laurate, decyl myristate, lauryl myristate, cetyl myristate, lauryl palmitate, cetyl palmitate, stearyl palmitate, cetyl p-t-butylbenzoate, stearyl 4-methoxybenxoate, dilauryl thiodipropionate, dimyristyl thiodipropionate, stearyl benzoate, benzyl stearyl, dibenzyl thiodipropionate, distearyl thiodipropionate, benzyl benzoate, glycerol trilaurate and so on.

The amount of the solvent may be in the range of 0 to 800 parts by weight, preferably 0.1 to 100 parts by weight, per part by weight of the acid-responsive chromogenic substance.

Most thermochromic dyes undergo a color change from a specific color to colorless (i.e., clear). Therefore, background color pigments can be provided in combination with the thermochromic compounds, such that when the thermochromic compounds change to colorless, the conventional or background pigments define the apparent color. For example, if a yellow pigment is mixed into the body lotion in combination with a red thermochromic dye, the visible color will appear to change from orange to yellow as the person steps into a hot shower; what is really happening is that the red thermochromic dye is changing from red to colorless.

Also within the contemplation of the invention are the thermochromic compositions of U.S. Pat. No. 5,919,404 (Fujita, et al.) entitled "Reversible Thermochromic Compositions" including a reversible thermochromic composition that has a reversible metachromatic function, that is, it presents a color-developed state when heated and presents the color-extinguished state when temperature-dropped or cooled in the color-developed state. The composition comprises as essential components (a) an electron-donating color-developing organic compound (b) at least one electron-accepting compound selected from alkoxyphenol compounds represented by a given formula, and (c) a compound such as paraffin wax serving as a reaction medium capable of reversibly causing electron-donating/accepting reaction attributable to the components (a) and (b).

It should be noted that thermochromics are reversible so that the effect is seen with each wash and not just the first.

Encapsulating of Thermochromic Materials

In the present invention, the reversibly variable color material can be directly blended with vehicle or can be encapsulated beforehand. The encapsulation can be carried out using the reversibly variable color material, a shell-forming polymer and, where necessary, a surfactant, protective colloid, pH control agent, electrolyte, etc. If microcapsules are desired, they can be prepared in water by any of interfacial polymerization, in situ polymerization, coacervation, air suspension, interfacial precipitation and other techniques. By such processes, microcapsules including the reversibly variable color material and measuring about 1 to 50 micrometers in diameter can be obtained. It is also possible to provide double- or multiple-walled microcapsules by using one, two or more of the microencapsulation techniques mentioned above. The preferred shell-forming material includes a polyamine and a carbonyl compound for a forming a polyurea shell, a polybasic acid chloride and a polyamine for forming a polyamide shell, a polyisocyanate and a polyhydroxy compound for a forming a polyurethane shell, a polybasic acid chloride and a polyhydroxy a compound for forming a polyester shell, an epoxy compound and a polyamine for forming an epoxy resin shell, a melamine-formaldehyde prepolymer for forming a melamine resin shell and a urea-formaldehyde prepolymer for forming a urea resin shell, as well as ethyl cellulose polystyrene, polyvinyl acetate and so on. The shell of said microcapsules is preferably made of a thermosetting material which is superior in heat resistance.

Thermochromatic pigments which are incorporated in a translucent or transparent encapsulate at up to 5% by wt. typically achieves the desired effect of noticeable color change. However, in less translucent carriers, higher levels (up to 35% by wt. pigment) can be included into the chips (e.g., encapsulates). Thus, range may vary from 0.1 to 35%, preferably 1 to 20% by wt.

Benefit Agent

To the extent that the dye may signal release of benefit agent at a given temperature, the bar composition also may comprise 0 to 25% by wt., preferably 1 to 20%, more preferably 2 to 15% by wt. benefit agent.

One class of ingredients are nutrients used to moisturize and strengthen the skin. These include:

a) vitamins such as vitamin A and E, and vitamin alkyl esters such as vitamin C alkyl esters;
b) lipids such as cholesterol, cholesterol esters, lanolin, creaminess, sucrose esters, and pseudo-ceramides;
c) liposome forming materials such as phospholipids, and suitable amphiphilic molecules having two long hydrocarbon chains,
d) essential fatty acids, poly unsaturated fatty acids, and sources of these materials, e) triglycerides of unsaturated fatty acids such as sunflower oil, primrose oil avocado oil, almond oil;

f) vegetable butters formed from mixtures of saturated and unsaturated fatty acids such as Shea butter;

g) minerals such as sources of zinc, magnesium, and iron;

A second type of skin benefit agent is a skin condition used to provide a moisturized feel to the skin. Suitable skin conditioners include.

a) silicone oils, gums and modifications thereof such as linear and cyclic polydimethylsiloxanes, amino, alkyl, and alkylaryl silicone oils;

b) hydrocarbons such as liquid paraffins, petrolatum, vaseline, microsrystalline wax, ceresin, squalene, pristan, paraffin wax and mineral c) conditioning proteins such as milk proteins, silk proteins and glutens;

d) cationic polymers as conditioners which may be used include Quatrisoft LM-200 Polyquaternium-24, Merquat Plus 3330—Polyquaternium 39; and Jaguar® type conditioners;

e) humectants such as glycerol, sorbitol, and urea f) emollients such as esters of long chain fatty acids, such as isopropyl palmitate and cetyl lactate;

A third type of benefit agent is deep cleansing agents. These are defined here as ingredients that can either increase the sense of refreshment immediately after cleansing or can provide a sustained effect on skin problems that are associated with incomplete cleansing. Deep cleansing agents include:

a) antimicrobials such as 2-hydrozy-4,2',4'-trichlorodiphenylether (DP300) 2,6-dimethyl-4-hydroxychlorobenzene (PCMX), 3,4,4'-trichlorocarbanilide (TCC), 3-trifluoromethyl-4,4'-dichlorocarbanilide (TFC), benzoyl peroxide, zinc salts, tea tree oil, b) anti-acne agents such as salicylic acid, lactic acid, glycolic acid, and citric acid, and benzoyl peroxide (also an antimicrobial agent), c) oil control agents including sebum suppressants, modifiers such as silica, titanium dioxide, oil absorbers, such as microsponges, d) astringents including tannins, zinc and aluminum salts, plant extracts such as from green tea and Witchhazel (Hammailes), e) scrub and exfoliating particles, such as polyethylene spheres, agglomerated silica, sugar, ground pits, seeds, and husks such as from walnuts, peach, avocado, and oats, salts, f) cooling agents such as menthol and its various derivatives and lower alcohols, g) fruit and herbal extracts, h) skin calming agents such as aloe vera, i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, methol, cineole, sugenol, citral, citronelle, borneol, linalol, geranoil, evening primrose, camphor, tymol, spirantol, penene, linonene and terpenoid oils.

Other benefit agents that can be employed include antiageing compounds, sunscreens, and skin lightening agents.

When the benefit agent is oil, especially low viscosity oil, it may be advantageous to pre-thicken it to enhance its delivery In such cases, hydrophobic polymers of the type described in U.S. Pat. No. 5,817,609 to He et al may be employed, which is incorporated by reference into the subject application.

Optional

In addition, the bar compositions of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers as conditioners which may be used include Quatrisoft LM-200 Polyquaternium-24, Merquat Plus 3330—Polyquaternium 39; and Jaguar® type conditioners.

Polyethylene glycols as conditioners which may be used include:

| | | |
|---|---|---|
| Polyox | WSR-205 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

Bar compositions of the invention also comprise from about 2 to 18%, preferably 3 to 15% water.

In a second embodiment of the invention, the bar comprises compositions made by combining chips made as described above (except they need not, and preferably do not, contain pigment since this will be in separate chip) with separate chip composition which is used for delivering the pigment and optionally benefit agent from the bar.

Release of benefit agent in final bar (whether from surfactant chip or pigment-containing chips) is cued by a change in the color of the thermochromatic pigment in the pigment-containing chip. Since release of benefit agent is tied to release of color, the color release is seen as a positive signal to the consumer rather than being perceived as only a dye with no other purpose.

The pigment-containing chip may comprise, for example:

(a) 40 to 99% typically 70 to 98% of a soluble structurant material (e.g., polyalkylene glycol of molecular weight about 4000 to 20,000)

(b) 0 to 40% by wt., typically 0 to 10% of chip benefit agent (e.g., silicone or other benefit agent which can be inside the chip on addition to the dye);

(c) 0.1 to 25% dye (samples having from 0.3-5% pigment/dye were made. Example 1 shows chips with 1.5 and 3% pigment, respectively, in a PEG chip; in Example 1, 10% of a 3% PEG chip were also mixed with 90% of a fatty acid soap chip to compare color change in release from concentrated region versus release when dye is dispersed throughout a 3% level)

(d) 0 to 10% by wt. water, preferably 0 to 5% by wt water (chip may comprise entirely structurant and chip would have no water).

The chip is typically pre-made and mixed with base noodles during a chip mixer or other low temperature addition process where the temperature does not exceed 40° C. when the bar is produced.

While a typical chip as noted is described, again it needs to be appreciated that any "system" for enveloping or surrounding the dye or pigment and ensuring it will be delivered in discrete domains can be used. This permits less of the dye to be used overall.

The final bar composition may be, for example, an extruded bar composition where 5 to 40% of the chips used are as noted above (e.g., PEG and pigment) and 95-60% of chips are chips comprising 5 to 90% by wt. of a surfactant system with surfactant selected from the group consisting of soap, anionic, nonionic, amphoteric, zwitterionic and cationic surfactant and mixtures thereof. Both soap and/or surfactant chips may comprise other additives typically found in such chips such as, for example, minor amounts of fragrance, preservative, skin feel polymer etc.

Although the surfactant system of the second (typically non-pigment containing) chip may be a pure soap surfactant system, preferably the surfactant system comprises:

(a) a first synthetic surfactant which is an anionic surfactant; and (b) a second synthetic surfactant selected from the group consisting of a second anionic different from the first, a nonionic, an amphoteric and mixtures thereof.

A particularly preferred surfactant system comprises acyl isethionate as the first anionic and a sulfosuccinate or a betaine surfactant or mixtures of the two.

Processing

The chip is typically pre-made by mixing the chip structurant material (e.g., polyethylene glycol of about 8000 molecular weight) with the thermochromic pigment (e.g., 1-3%) above the melting temperature of the polymer. The material is then typically cast onto a chill roll where the material forms a solid and is turned into flakes at the knife edge. The flakes are then mixed with base noodles (e.g., soap or non-soap surfactant-based noodles) during a chip mixer or other low temperature addition process (excess working that gives rise in material temperature and could lead to intimate mixing should be avoided) where the temperature does not exceed 40° C. when the bar is produced.

EXAMPLES

Protocol

PEG 8000 was melted at 10000 in a Patterson mixer. 1-3% Thermochromic pigment (Cleveland Pigments and Color, TCP) powder was added to the mixer until the pigment was mixed in thoroughly. The liquid batch was chill-rolled at −5° C. until solid and was then flaked into chips or cast onto a cooled metal sheet to create thicker chip samples which were more suited for color measurements.

The above dye-containing chips were mixed into bar base material (comprising, for example, fatty acid soap) at 10% (to give 0.1-0.3% pigment in the total formulation) at 25-30° C.—below the chip melting temperature; and then extruded and stamped. Without recycling, the mixing was insufficient to intimately mix the pigment-containing chip into the base material. With multiple recycling passes, the chip mixed into the base such that the entire bar was homogeneously colored.

To test the color change on heating, the PEG chips containing pigment were tested using a Hunter Lab Scan XE reflectometer where L*=black to white (luminance), measured on a 0-100 scale; a*=green to red (0-60 scale), b*=blue to yellow (0-60 scale); and $\Delta E=[(\Delta L^*)^2+(\Delta a^*)^2+(\Delta b^*)^2]^{0.5}$. ΔE is defined as total difference of (CIE) 1976 L*a*b* scale. It is a simple cube root version of the Adams-Nickerson space produced by plotting the quadrants of the L*a*b* in rectangular coordinates. The chips were laid flat over a 0.5" aperture and covered with a white sample cover that excluded external light. The initial reading is taken at room temperature as baseline. The second reading is taken immediately after the sample has been exposed to warm water (>40° C.) for about 1 minute.

The results are shown in FIG. 1.

Example 1

Primarily Anionic Base

A bar composition comprising the following components was prepared:

| Ingredient | Range by wt. |
|---|---|
| Anionic Surfactant (e.g., sodium cocoyl isethionate) | 40-60% |
| Free fatty acid (e.g., $C_{14}$-$C_{16}$ fatty acid) | 25-30% |
| Amphoteric (cocoamidopropyl betaine) | 1-5% |
| Structurant (e.g., sodium stearate) | 0-10% |
| Mildness enhancer (sunflower oil) | 2-8% |
| Unencapsulated dye or pigment | 0.1-5% |
| Water | 3-16% |

Such a bar would typically be made by using single chip (not blend of chips) and, since such chips could be found through the bar, the final bar, when dye is released, would have a uniform color (dependent on what dye is used). For example, if dye is a blue dye and base was initially white, upon release of dye, the bar appears uniformly blue (i.e., turns from white to blue).

Example 2

Lower Amount of Surfactant Base

Another bar composition which can be used is similar to Example 1, but comprises less anionic (20 to 40%) and uses 10 to 50%, preferably 10 to 40% of a water soluble structurant with melting point 40° C. to 100° C. (e.g., polyalkylene oxide, copolymers of polyethylene and polypropylene oxide) to act as structurant rather than more water insoluble fatty acid structurant such as $C_{16}$-$C_{18}$ fatty acid. Examples of such bars are noted, for example, in U.S. Pat. No. 6,028,042 to Chambers.

A typical bar composition may comprise

| Ingredient | Range by wt. |
|---|---|
| Anionic Surfactant (e.g., sodium cocoyl isethionate) | 20-40% |
| Water soluble structurant (e.g., PEG) | 15-35% |
| Free fatty acid ($C_{14}$/$C_{16}$) | 15-25% |
| Amphoteric (e.g., betaine) | 1-7% |
| Non-water soluble structurant (e.g., sodium stearate) | 2-12% |
| Mildness enhancer (e.g., sodium isethionates) | 5-10% |
| Dye | 0.1-3% |
| Water | 3-15% |

Bars of Examples 1 or 2 are typically made by mixing compounds in a molten stage, chilling to form chips, optionally milling, plodding and stamping. Alternatively, liquid mixture can be cast into a mold in a cast mold process.

Again, the bar of this example would be made from a single dye-containing chip rather than from a blend comprising dye containing chips and non-dye containing chips. Therefore, because chips are found throughout the bar, when the dye is released, the bar would have a uniform color (with color dependent on which dye is released). Thus again, an initially white bar would turn uniform blue upon release of dye at the appropriate dye-release temperature.

Example 3

Soap based Bar

Bars of the invention may also be pure soap-based bars comprising for example:

| Ingredient | Range by wt. |
|---|---|
| Soap | 60-90% |
| Water | 3-12% |
| Dye | 1-10% |
| Perfumes, germicides, colorants, pigments and other minors | To 100% |

Again, like bars of Example 1 and 2, this bar is typically made from a single dye-containing chip and, when dye is released, the bar will have uniform color.

Example 4

Mixed Chip Processing

If using a separate pigment chip mixed with base chip, typically the process is conducted as follows:

The chip with dye in the chip can be formed by mixing, for example, polyalkylene glycol, dye and water, if any, at a temperature above melting point of polyalkylene glycol (e.g., >50° C.) for 1-60 minutes and cooling on chill roll. The non-dye containing chip similarly is formed by mixing ingredients at elevated temperature and cooling, Chips can then be combined, for example, in a low temperature (e.g., below about 40° C.) hopper or mixer where they may be refined, are then plodded into billets, stamped and cut. It is important that chips are mixed at low temperature because this ensures they are not uniformly mixed and that therefore, regions are formed where there are more dye-containing chips than other regions. These are so called "concentrated" regions (although, of course, any single dye-containing chip will be more concentrated when any single non dye-containing chip if it really has no dye).

It should be noted that what we are calling the "non-dye containing chip" could typically have some dye. However, since these chips are found throughout the bar, it would defeat the purpose of having concentrated dye regions (associated with the separate pigment chip) since some dye would be released from all chips.

On the other hand, it should also be noted that the dye in the "non-dye containing chip" can be a different color than the dye in the "pigment chip" so that one could make a bar which, when dyes are released, one would obtain a base of one color and concentrated regions of a different color.

Example 5

In order to show general advantage of using mixed chips (for localized pigment) rather than uniformly distributing pigment when one bar base is used (as in Examples 1-3), applicants created Chips A and Bars B & C as follows: (Bar D is prophetic)

Chips A: Polyalkylene chips w/3% pigment which were mixed with bar base at 10% by weight (total pigment is 0.3% by weight of the formulation); Since the base bar chips have no dye in this example, the final bar contained blue concentrated areas (pigment turned blue on release) on a white bar base;

Bar B: A bar similar to that of Example 1 (predominantly synthetic and containing no dye in the base chip) where 10% of the polyalkylene glycol (e.g., PEG 4000-8000) chips which contain 3% thermochromic dye were uniformly mixed at temperature >45° C. to eliminate localization of pigment in discrete chip domains (total pigment is 0.3% by weight of the formulation). In this case, because the chips were mixed at sufficiently high temperature, uniform mixture is obtained and even though a blend of chips is used, the dye will release uniformly throughout the bar rather than create speckled regions;

Bar C: A pure soap bar (as in Example 3) wherein 10% PEG chips which contain 3% thermochromic dye were uniformly mixed (total pigment is 0.3% by weight of the formulation); again, the chips are mixed at temperature high enough that uniform mixing and uniform dye release will occur;

Bar D: A pure soap bar (as in Example 3) wherein 0.3% thermochromic dye is uniformly mixed into the base; here there is single chip used again and, upon release of chip, uniform color would be seen.

The results for various parameters (L, a, b, ΔE, Δa, ΔL, Δb) for select examples of dye in various PEG chips (one with 3% pigment and three with 1.5% pigment)), as well as for dye in full bars, are set forth in the Table below as well as graphically set forth in FIG. 1.

| | | L | a | b | ΔE | Δa | ΔL | Δb |
|---|---|---|---|---|---|---|---|---|
| Chip A (1) | 3% thermochromic in PEG chip (RT) | 41.84 | −5.56 | −22.85 | | | | |
| | 3% thermochromic in PEG chip (40° C.) | 66.28 | −6.21 | −2.55 | 31.77 | −0.65 | 24.44 | 20.29 |
| Chip A (2) | 1.5% thermochromic in PEG chip (RT) | 39.51 | −6.34 | −26 | | | | |
| | 1.5% thermochromic in PEG chip (40° C.) | 65.02 | −4.52 | 0.46 | 36.8 | 1.82 | 25.51 | 26.45 |
| Chip A (3) | 1.5% thermochromic in PEG chip (RT) | 38.1 | −5.83 | −25.63 | | | | |
| | 1.5% thermochromic in PEG chip (40° C.) | 67.01 | −5.04 | 1.53 | 39.67 | 0.79 | 28.91 | 27.16 |

-continued

| | | L | a | b | ΔE | Δa | ΔL | Δb |
|---|---|---|---|---|---|---|---|---|
| Chip A (4) | 1.5% thermochromic in PEG chip (RT) | 38.73 | −6.21 | −25.88 | | | | |
| | 1.5% thermochromic in PEG chip (40° C.) | 66.25 | −5.03 | 1.25 | 38.67 | 1.19 | 27.53 | 27.14 |
| Bar B | 0.3% thermochromic in bar of Example 1, uniformly distributed (RT) | 77.39 | −5.25 | −10.74 | | | | |
| | 0.3% thermochromic in bar of Example 1, uniformly distributed (40° C.) | 86.33 | −4.08 | −1.79 | 12.71 | 1.17 | 8.95 | 8.95 |
| Bar C | 0.3% thermochromic in bar of Example 3, uniformly distributed (RT) | 78.26 | −7.06 | −6.89 | | | | |
| | 0.3% thermochromic in bar of Example 3, uniformly distributed (40° C.) | 84.44 | −5.22 | 2.24 | 11.18 | 1.84 | 6.18 | 9.13 |

Bar D example not actually prepared,

As clearly seen from ΔE values, for example, the color change in localized chip (the 3% dye in PEG chip and three examples of 1.5% dye in PEG chips of A(1), A(2) A(3), and A(4)) is much greater than if pigment is dispersed uniformly throughout a bar composition (Bars (B) and (C) of Example 5), whether or not the bar composition is synthetic or pure soap.

It should be noted that a key difference between data relating to chips A(1), A(2), A(3) and A(4) compared to Bar B and Bar C is that chips A capture release from localized chip, while Bar B and Bar C, because the dye chips are uniformly mixed and found throughout the bar, capture the data based on release from uniform, dispersed, chip distribution. In chips A(1)-A(4), the measured ΔE was taken of the chip only (this was the only area where dye was released), while for bars (B) and (C), ΔE was measured from the whole bars (since dye was released uniformly throughout bar).

It can be seen from the example that a preferred embodiment of the invention related to bars with concentrated amounts of dye (concentrated domains) where, to ensure such concentrated domains are formed, chips are not "uniformly" mixed (i.e., not mixed at temperature >45) in order to distribute the pigment chip throughout the bar).

The invention claimed is:

1. Solid bar composition comprising:

(a) 5 to 85% by wt. of a surfactant selected from the group consisting of anionic surfactant, nonionic surfactant, amphoteric surfactant, cationic surfactant and mixtures thereof;

(b) 1 to 50% by wt. bar structurant;

(c) 0 to 30% by wt. free fatty acid;

(d) 0.1 to 10% by wt. thermochromatic pigment or dye; and (e) 1 to 25% benefit agent wherein said bar comprises combining chip compositions comprising i. (a) 40 to 99.9% by wt. chip composition of a polyalkylene glycol soluble structurant material;

(b) 1 to 40% by wt. chip composition of a benefit agent;

(c) 0.1 to 25% by wt. chip composition thermochromatic pigment; and (d) 0 to 10% by wt. chip composition water; and ii. 95 to 60% by wt. chips comprising surfactants;

wherein (i) and (ii) are combined to form said final solid bar composition in which the pigment is found in the final bar in concentrated regions defined by the chips of (i).

2. A composition according to claim 1, additionally comprising 1-25% mildness enhancer.

3. A composition according to claim 2, wherein said enhancer is alkali metal isethionate.

4. A composition according to claim 1, wherein the surfactant-containing chips of subparagraph (ii) comprise no thermochromatic pigment.

* * * * *